United States Patent [19]

Hardy et al.

[11] Patent Number: 5,897,862
[45] Date of Patent: Apr. 27, 1999

[54] IMMUNO-STIMULATORY MONOCLONAL ANTIBODIES

[75] Inventors: Britta Hardy, Tel Aviv; Avraham Novogrodsky, Rehovot, both of Israel

[73] Assignee: Mor Research Applications Ltd., Israel

[21] Appl. No.: 08/380,857

[22] Filed: Jan. 30, 1995

[30] Foreign Application Priority Data

Jan. 31, 1994 [IL] Israel ........................................ 108501

[51] Int. Cl.$^6$ ............................ C07K 16/28; C12N 5/12; A61K 39/395

[52] U.S. Cl. ................... 424/153.1; 435/332; 435/343.1; 424/152.1; 530/388.2; 530/388.7; 530/388.73

[58] Field of Search ........................... 530/387.14, 388.2, 530/388.7, 388.73; 435/240.27, 332, 343.1; 424/152.1, 153.1

[56] References Cited

U.S. PATENT DOCUMENTS 5,182,368  1/1993  Ledbetter .

OTHER PUBLICATIONS

Osband and Ross, Immunology Today 11: 193–195 1990.
Hoskins et al., Cancer Immunol Immunother 29:226–230, 1989.
Brown et al, Blood 73: 651–661, 1989.
Hird and Epenetos, Ch 17 "Immunotherapy with Monoclonal Antibodies" in Genes and Cancer, Ed by Carney & Sikora, 1990 John Wiley & Sons, pp. 183–189.
Clark, Edward A. et al., "Amplification of the Immune Response by Agonistic Antibodies," *Immunology Today*, vol. 7, No. 9, 1986.
Meuer, Stefan C. et al., "Triggering of the T3–Ti Antigen–Receptor Complex Results in Clonal T–cell Proliferation Through an Interleukin 2–Dependent Autocrine Pathway," *Proc. Natl. Acad. Sci. USA*, vol. 81, pp. 1509–1513, Mar. 1984.

Van Wauwe, Jean P. et al., "OKT3: A Monoclonal Anti–Human T Lymphocyte Antibody With Potent Mitogenic Properties," *The Journal of Immunology*, vol. 124, No. 6, Jun. 1980.
Jung, Gundram et al., "Induction of Cytotoxicity in Human Peripheral Blood Mononuclear Cells by Monoclonal Antibody OKT3" *The Journal of Immunology*, vol. 139, No. 2, pp. 639–644, Jul. 15, 1987.
Van Lier, R. et al., "Studies on the Monocyte Dependence of T–Cell Proliferation Induced by Monoclonal Antibodies Directed Against Regions I and II of the CD2 Antigen," *Immunology*, vol. 67, pp. 333–338, 1989.
Ellenhorn, Joshua D. et al., "In Vivo Administration of Anti–CD3 Prevents Malignant Progressor Tumor Growth," *Science* (Washington, D.C.), vol. 242, pp. 569–571, Oct. 1988.
Gallinger, Steven et al., "Comparison of Cellular Immunotherapies and Anti–CD3 in the Treatment of MCA–38–LD Experimental Hepatic Metastases in C57BL/6 Mice," *Cancer Research*, vol. 50, pp. 2476–2480, 1990.
Ledbetter, Jeffrey A. et al., "Antibodies to Tp67 and Tp44 Augment and Sustain Proliferative Responses of Activated T Cells," *The Journal of Immunology*, vol. 135, No. 4, 2331–2336, Oct. 4, 1985.
Moretta, Alessandro et al., "CD69–mediated Pathway of Lymphocyte Activation: Anti–CD69 Monoclonal Antibodies Trigger the Cytolytic Activity of Different Lymphoid Effector Cells with the Exception of Cytolytic T Lymphocytes Expressing T Cell Receptor $\alpha/\beta$," *J. Exp. Med.*, vol. 174, pp. 1393–1398, Dec. 1991.
Van Lier, Reneé A. W. et al., "Signals Involved in T Cell Activation. T Cell Proliferation Induced Through the Synergistic Action of Anti–CD28 and Anti–CD2 Monoclonal Antibodies," *Eur. J. Immunol*, vol. 18, pp. 167–172, 1988.
Jenkins, Marc K. et al., "CD28 Delivers A Costimulatory Signal Involved In Antigen–Specific IL–2 Production by Human T. Cells," *The Journal of Immunology*, vol. 147, No. 8, pp. 2461–2466, Oct. 15, 1991.
Townsend, Sarah E. et al., "Tumor Rejection After Direct Costimulation of CD8$^+$ T Cells By B7–Transfected Melanoma Cells," *Science* (Washington, D.C.), vol. 259, pp. 368–370, Jan. 15, 1993.
Hardy, Britta et al., "A Monoclonal Antibody to Human B Lymphoblastoid Cells Activates Human and Murine T Lymphocytes," *Cellular Immunology*, vol. 118, pp. 22–29, 1989.

Hardy, Britta et al., "A Monoclonal Antibody Against a Human B Lymphoblastoid Cell Line Induces Tumor Regression in Mice," *Cancer Research,* vol. 54, pp. 5793–5796, Nov. 15,1994.

*Primary Examiner*—Paula K. Hutzell
*Assistant Examiner*—Nancy A. Johnson
*Attorney, Agent, or Firm*—Gary M. Nath; Suet M. Choung; Nath & Associates

[57] ABSTRACT

A monoclonal antibody having immuno-stimulatory effects, binds specifically to B lymphoblastoid cells and induces proliferation and activation of peripheral blood lymphocytes, and when injected into tumor-bearing animals elicts an anti-tumor effect.

9 Claims, 14 Drawing Sheets

FIG. 3E
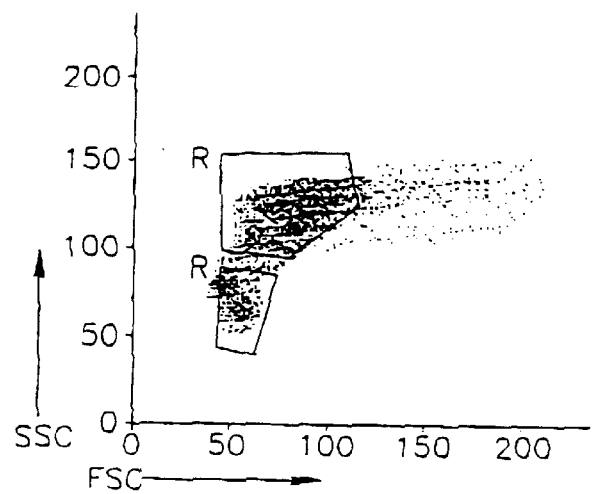
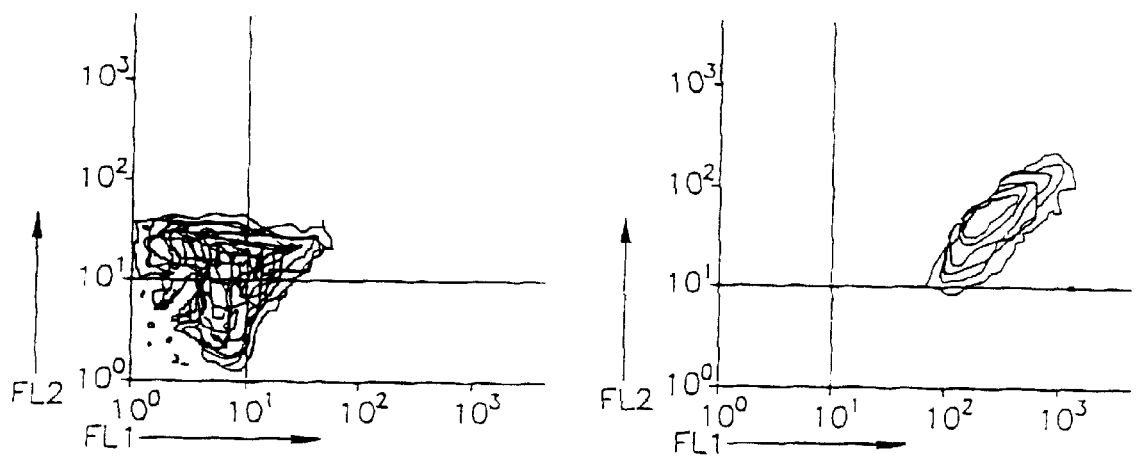
FIG. 3F  FIG. 3G

IMMUNO-STIMULATORY MONOCLONAL ANTIBODIES

FIELD OF THE INVENTION

The present invention is generally in the field of immunotherapy and more specifically concerns monoclonal antibodies useful within the framework of such a therapy for a variety of indications, e.g., in the treatment of cancer.

PRIOR ART

The following is a list of prior art references considered to be pertinent for the subsequent description:

1. Clark, E. A., and Ledbetter, J. A., Amplification of the immune response by agonistic antibodies, *Imunol., Today*, 7:267–270, 1986.
2. Meuer, S. C., Huspey, R. E., Cantrell, D. A., Hodgdon, J. C., Schlomman, S. F., Smith, K. A. and Reinberg, E. L., Triggering of the T3-T1 antigen-receptor complex results in clonal T cell proliferation through an interleukin-2 dependent autocrine pathway, *Proc. Natl. Acad. Sci.* (USA), 31:1509–1513, 1984.
3. Van Wauve, J. P., De Mey, J. R., and Gooser, J. G., OKT3: a monoclonal anti-human T lymphocyte antibody and potent mitogenic properties, *J. Immunol.*, 124:2708–2713, 1980.
4. Jung, G., Martin, D. E., and Muller-Eberhard, J. H., Induction of cytotoxicity in human peripheral blood mononuclear cells by monoclonal antibody OKT3, *J. Immunol.*, 139 639–644, 1987.
5. Van Lier, R., Blocmena, E., Brouwer, M., Van Heijm, J., Weinreich, S., and Aarden, L., Studies on the monocyte dependence on T-cell proliferation induced by monoclonal antibodies directed against region I and II of CD2 antigen, *Immunology*, 67:333–338, 1989.
6. Ellenhorn, J. D., Hirsch, R., Schreiber, H. and Bluestone, J. A., In vivo administration of an anti-CD3 prevents malignant progressor tumor growth, *Science* (Washington, D.C.), 242:569–571, 1988.
7. Gallinger, S., Hoskins, D. W., Mullen, J. B. M., Wong, A. H. C., and Roder, J. C., Comparison of cellular immunotherapies and anti-CD3in the treatment of MCA-38-LD experimental hepatic metastases in C57BL/6 mice, *Cancer Res.*, 50:2476–2480, 1990.
8. Ledbetter, J. A., Martin, P. J., Spooner, C. E., Wofsy, D., Tsu, T. T., Beatty, P. G., and Gladstone, P., Antibodies to Tp67 and Tp44 augment and sustain proliferation responses of activated T cells., *J. Immunol.*, 135:2331–2336, 1985.
9. Moretta, A., Goggi, A., Pende, D., Tripodi, G., Orengo., A., Pella, N., Augugliaro, R., Bottino, C., Ciccone, E., and Moretta, L., CD69-mediated pathway of lymphocyte activation: anti-CD69 monoclonal antibodies trigger the cytolytic activity of different lymphoid effector cells with the exception of cytolytic T lymphocyte expressing T cell receptor α/β, *J. Exp. Med.*, 174;1393–1398, 1991.
10. Van Lier, R. A., Brouwer, M., and Aarden, L. A., Signals involved in T cell activation. T cell proliferation induced through the synergistic action of anti-CD28 and anti-CD2 monoclonal antibodies, *Eur. J. Immunol*, 13:167–172, 1988.
11. Jenkins, M. K., Taylor, P. S., Norton, S. D., and Urdahl, K. B. CD28 delivers a costimulatory signal involved in antigen-specific IL-2 production by human T cells, *J. Immunol.*, 147:2461–2466, 1991.
12. Townsend, S. E., and Allison, J. P., Tumor rejection after direct costimulation of CD8+ T cells by B7-transfected melanoma cells, *Science* (Washington, D.C.), 259:368–370, 1993.
13. Hardy, B., Dotan, D., and Novogrodsky, A., A monoclonal antibody to human B lymphoblastoid cells activates human and murine T lymphocytes, *Cell Immunol.*, 118:22–29, 1989.

The acknowledgement herein of any of the above references is to allow the reader to gain appreciation of the prior art. The acknowledgement should, however, not be construed as an indication that these references are in any way relevant to the issue of patentability of the invention as defined in the appended claims.

Acknowledgement of the above references will be made by indicating the number from the above list.

BACKGROUND OF THE INVENTION

Cancer in its different forms is a major cause of death in humans. One-third of all individuals in the United States develop cancer and 20% die from cancer (494,000 in 1988).

The most widely used therapeutic treatments of cancer are surgery, radiation and chemotherapy. In recent years, another therapeutic treatment based on use of biological response modifiers (BRM) has also been proposed. The BRMs used include mainly cytokines (e.g., Interleukin-2 (IL-2) and Interferon-α (INF-α)), activated mononuclear cells (e.g., lymphokine activated killer cells (LAK)) and antibodies. The BRMs act both directly on tumors and indirectly by enhancing non-specific or specific immunological and cytotoxic mechanisms.

To date, no substantial clinical success has been obtained using BRMs, mainly due to their toxicity and side effects. Active immunization against tumor cancer has also been proposed but found ineffective. Furthermore, several monoclonal antibodies (mAbs) were evaluated for use in diagnosis and therapy of cancer but no mAb has yet proven to be effective within a standard therapeutic procedure in cancer patients.

Various mAbs capable of binding to determinants on the surface of T cells have been found to induce proliferation, activation or differentiation of these cells[1]. Binding of mAbs directed against the CD3/TCR complex on T cells [2–4], binding of mAbs directed at the CD2[5] receptor antigen on T cells as well as binding of both above kinds of antibodies to T cells, have been demonstrated to bring about T cell proliferation, IL-2 receptor expression and IL-2 production in T cells resulting in the enhancement of the cytolytic process in these cells. The anti CD3 mAb was shown to initiate an anti tumor activity in vivo in an animal model[6–7].

Various other mAbs directed against T-lymphocyte antigens have also been reported which, after binding to the cells, cause their activation such as mAbs directed against CD5[8], against CD69[9] and against CD28[10,11]. Anti-CD28 mAbs were reported to have decreased the rate of growth of a murine melanoma although they were not successful in completely eliminating the tumors in the mice[12].

A mAb directed against a human B lymphoblastoid cell line termed "Daudi" was shown to stimulate murine lymphocytes and human peripheral T cells[13].

GENERAL DESCRIPTION OF THE INVENTION

The present invention provides, by a first of its aspects, a monoclonal immuno-stimulatory antibody, which binds to B lymphoblastoid cells and induces proliferation and activation of peripheral blood lymphocytes, the monoclonal antibody being characterized in that when injected into a tumor-bearing animal, it elicits an anti-tumor effect.

An anti-tumor effect is a biological effect which can be manifested by a decrease in tumor size, a decrease in the number of metastases, an increase in life expectancy, or amelioration of various physiological symptoms associated with the cancerous condition. An anti-tumor effect can also be manifested by the ability of the mAb in prevention of the occurrence of tumor in the first place. Given its properties, the mAb of the invention can be used both in the treatment of acute cancer as well as in cancer prophylaxis.

The monoclonal antibodies of the invention can be obtained by first immunizing an animal with an immunogen, being B lymphoblastoid cells, lysed B lymphoblastoid cells or membrane preparations thereof. Following immunization and the development of an immune reaction in the immunized animals, B-lymphocytes are withdrawn from the animal, lines are grown and selected for such with secrete antibodies which bind to the immunogen. The selected mAbs are then subjected to a further selection for such capable of inducing proliferation and activation of peripheral blood lymphocytes.

In order to obtain the mAbs of the invention, the antibodies selected as above, are then subjected to a still further selection for such capable of eliciting an anti-tumor effect. In order to select such antibodies, typically an animal model of cancer can be used. At times the effect may also be tested in various in vitro models. Such a model may, for example, be any laboratory animal in which cancer has been induced. Specifically relevant, particularly for choosing a mouse for therapeutic use in humans, are models allowed to develop human-originated tumors. Examples of animal models of the latter type are immuno compromised mice, e.g. a SCID mouse or a nude mouse which have been injected or implanted with tumor cells or tissue obtained from human cancer patients. In such selection, the ability of the mAb to reduce the tumor size, increase survival time, etc., is determined as compared to control (a similar tumor-bearing animal not treated with the mAb or treated with a non relevant mAb).

The selection may also involve testing in an appropriate model, of the mAb's ability in preventing the occurrence of cancer. For example, animals having a genetic predisposition for developing cancer may be injected with the mAb and then the tumor incidence and the survival in the group treated with the mAb can be compared to a control group, otherwise treated and maintained in the same manner. Rather than using animals having a genetic predisposition, the ability of the mAb to prevent cancer can be tested in various other animals treated with the mAb prior to experimental administration of malignant cells in the animal.

In order to achieve such an anti-tumor effect, the subject has to be administered with an effective amount of the mAb of the invention. The term "effective amount" should be understood as meaning an amount of a mAb required to achieve a therapeutic effect. The effective amount required to achieve the therapeutic end result may depend on a number of factors including, for example, the tumor type and the severity of the patient's condition (i.e. the cancerous state), and whether the mAb is co-administered together with another agent which acts together with the mAb in an additive or synergistic manner (regarding such co-administration, see below).

The obtaining of an immortalized cell line secreting mAbs of the invention can be performed by a number of means known per se, such as by fusion with an immortalized cell line to yield a hybridoma; by EBV transformation; by genetically engineering a cell line, e.g. a CHO cell line, which can be achieved by a variety of means known per se; etc. In general, the manner of obtaining immortalized monoclonal antibody secreting cell lines is today a routine procedure known to the artisan and the description thereof goes beyond the present writing.

Typically, where the mAb is intended for treatment in a human, the immunogen will be of a human origin. However, at times there is an inter-species cross reactivity and it is also possible, occasionally, to use in humans mAbs obtained following immunization with a non-human derived immunogen, as the e.g., primate derived.

The antibodies of the invention should be understood as encompassing monoclonal antibodies, which may be IgG or IgM antibodies, may be Fab fragments of such antibodies, $F(ab')_2$ fragments, single chain antibodies, and the like. In addition, antibodies derived from a non-human origin, e.g. murine, may be "humanized" by various genetic engineering means (a "humanized" antibody is an antibody in which major portions have been replaced with portions of a human origin).

Antibodies in accordance with the invention, while being useful for a variety of therapeutic indications, are used, in accordance with a preferred embodiment of the invention, for the treatment of cancer. It has been found that a monoclonal antibody in accordance with the invention is active in reducing tumorigenicity of a variety of tumors.

A representative hybridoma cell line in accordance with the present invention was deposited at the Collection Nationale de Cultures de Microorganismes (CNCM), Institute pasteur, 25, Rue du Docteur Roux, 75724, Paris, Cedex 15, under Deposit Accession No. I-1397, on Jan. 28, 1994. The cells of this line are referred to herein at times as "BAT-1 cells", and the respective monoclonal antibody is referred to herein at times as "BAT-1 mAb".

Use of a monoclonal antibody having the characteristics of the BAT-1 mAb, specifically the BAT-1 mAb itself, is a preferred embodiment of the invention.

The BAT-1 monoclonal antibody was selected on the basis of its binding to cells of the Daudi human B lymphoblastoid line. The BAT-1 mAb was found to bind to a proteinaceous substance (termed below as "BAT-1 binding protein") having an apparent molecular weight of 48–50 K Daltons, as determined by SDS-PAGE.

The BAT-1 binding protein forms another aspect of the present invention. The BAT-1 binding protein may be isolated, by various means known per se by using the mAbs of the invention. The BAT-1 binding protein may then be used for immunization of animals from which mAbs of the invention may then be derived.

The present invention also provides a pharmaceutical composition comprising, as an active ingredient, an effective amount of an mAb of the invention, and a physiologically acceptable carrier.

A further aspect of the invention is a method of treatment of a disease or disorder, particularly cancer, comprising administering to a subject in need an effective amount of the inventive mAb. The administration of the mAb is typically by means of parenteral administration, e.g., intravenously (i.v.) intraperitoneally (i.p.) or intramuscularly (i.m.). The carrier for administration may be any one of such known per se, e.g., a saline solution or any other suitable physiological solution.

The mAb of the invention was found, as already noted above, to be active in reducing tumorigenicity of a variety of tumors. The efficacy of the mAb of the invention in reducing tumorigenicity is correlated with its ability to induce cytotoxic activity of lymphocytes. In order to boost up this activity, it is at times advantageous to administer the mAb of the invention together with other agents which can act in an additive or synergistic manner with the mAb. Examples include various cytokines such as IL-1 (Interleukin-1), IL-2, IL-6 and IFN-α (Interferon-α).

The mAb of the invention may be useful in the therapy of a variety of diseases other than cancer where activation or other effects of the mAb on the immune system's cytotoxic activity may have a therapeutic effect, such as, for example, in early stages of HIV infection (the causative virus of acquired immune deficiency—AIDS), in various autoimmune disorders, or in some cases of genetic or acquired immune deficiencies.

In the treatment of cancer the antibody may be administered either following detection of primary or secondary tumors in the subject or, in preventive therapies of subject having a high risk of developing cancers, such as an individual exposed to radiation or such having a genetic disposition. Similarly, in AIDS patients, the mAb may be administered to infected individuals, which have not yet developed any symptoms of the disease, or in individuals at early stages of the HIV infection process.

In the following, the invention will be illustrated by various examples describing experiments demonstrating the anti-cancer therapeutic activity. It should, however, be understood that this is meant for illustration purposes only and is not to be considered limiting.

BRIEF DESCRIPTION OF THE DRAWINGS

FIG. 1A—background reading without BAT antibody;
FIG. 1B—anti-CD3 antibody;
FIG. 1C—BAT-1;
FIG. 1D—BAT-5;
FIG. 1E—BAT-2;
FIG. 1F—BAT-4.

FIG. 2A–2D—ungated cells;
FIG. 2A—PBM cells treated with BAT mAb;
FIG. 2B—PBM cells treated with anti-CD3 mAb;
FIG. 2C—Jurkat T cells treated with BAT mAb;
FIG. 2D—Jurkat T cells treated with anti-CD3;
FIG. 2E–2I—gated cells;
FIG. 2E—PBM cells gated to small (R1) and large cells (R2);
FIG. 2F—(R1) cells treated with BAT mAb;
FIG. 2G—(R1) cells treated with anti-CD3;
FIG. 2H—(R2) cells treated with BAT mAb;
FIG. 2I—(R2) cells treated with anti-CD3.

FIG. 3A–3G show a flow cytometry analysis of surface expression of BAT binding protein and CD3 on human PBM double labeled with FITC-conjugated BAT mAb and PE-conjugated anti-CD3.

FIG. 3A–3D—ungated cells;
FIG. 3A—Becton-Dickinson simultest control, used as a negative control;
FIG. 3B—PE-anti-CD3 alone;
FIG. 3C—FITC-BAT mAb alone;
FIG. 3D—Double labelling with both FITC-BAT mAb and PB-anti-CD3 antibody;
FIG. 3E–3G—Gated cells;
FIG. 3E—PBM cells gated to small (R1) and large cells (R2);
FIG. 3F—(R1) cells double labeled with FITC-BAT mAb and PE-anti CD3;
FIG. 3G—R2) cells double labeled with FITC-BAT mAb and PE-anti CD3.

FIG. 4A—lysates from Daudi cells (untreated);
FIG. 4B—lysates treated with neuraminidase (0.2 u/ml);
FIG. 4C—lysates treated with neuraminidase (0.4 u/ml);
FIG. 4D—lysates treated with Endo Hf (100 u/μg).

MATERIALS AND METHODS

Production of Monoclonal Antibodies

Figure 1A:
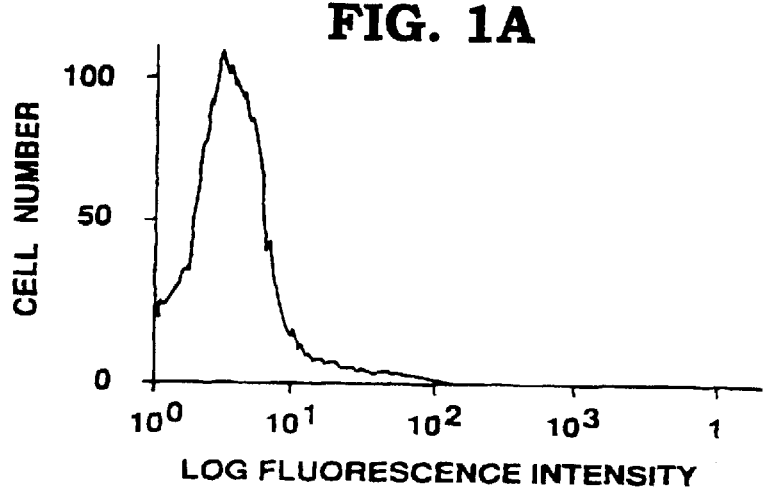
FIG. 1A–1F shows flow cytometry analysis of binding of BAT monoclonal antibodies (mAbs) to human purified T-lymphocytes. Binding of the BAT antibodies was assessed by a second antibody carrying a fluorescent marker, FITC-goat anti-mouse antibody.
Figure 1B:
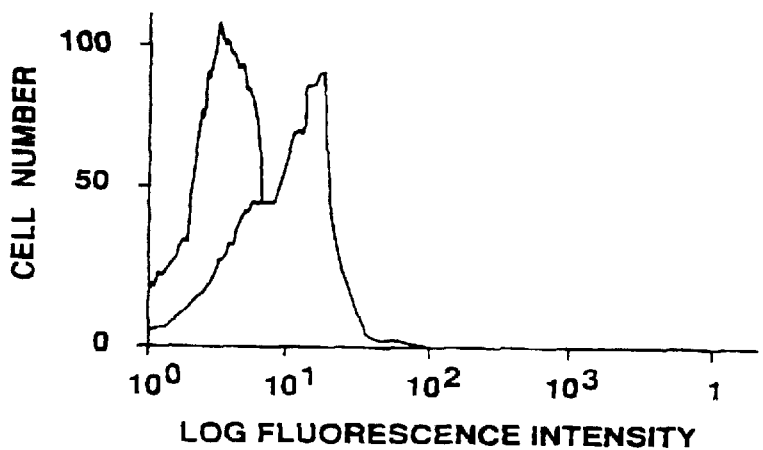
Figure 1C:
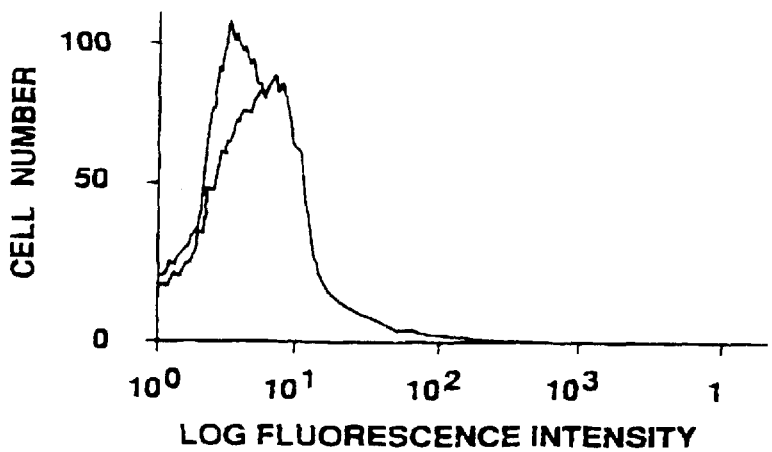
Figure 1D:
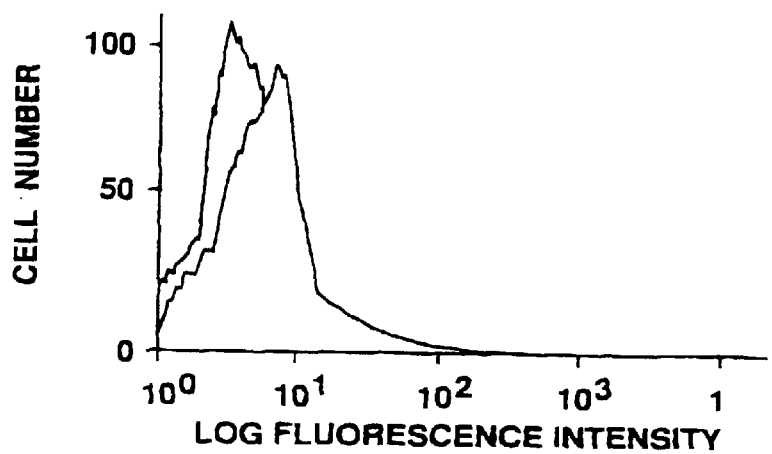
Figure 1E:
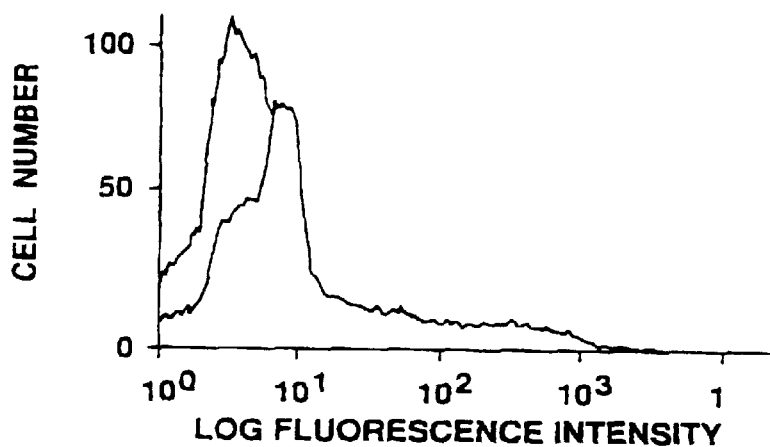
Figure 1F:
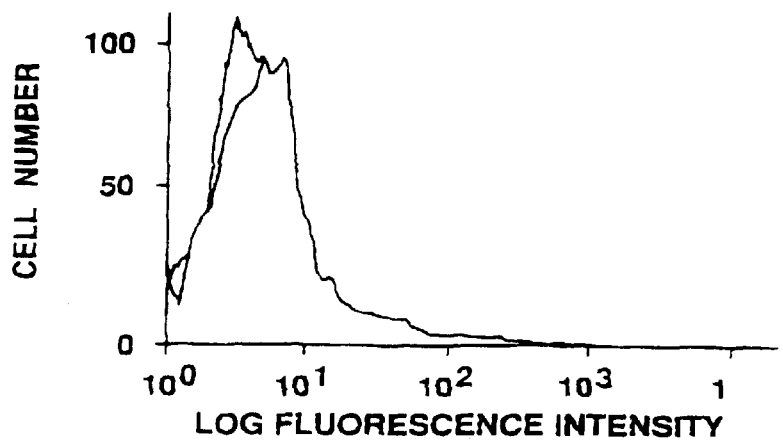
Figure 2A:
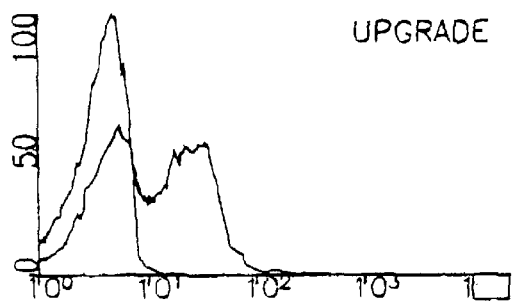
FIG. 2A–2I show a flow cytometry analysis of human peripheral blood monocytes (PBM) (left plate) and of Jurkat T cells (right plate) double labeled with primary antibody being either a BAT mAb or an anti CD3 mAb and a second FITC conjugated anti-mouse IgG antibody.
Figure 2B:
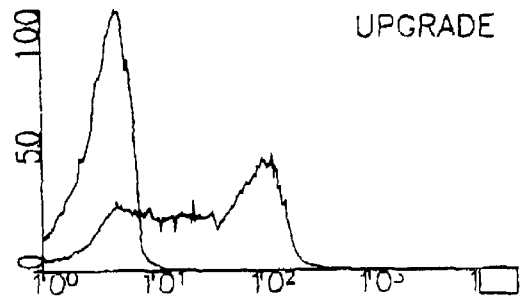
Figure 2C:
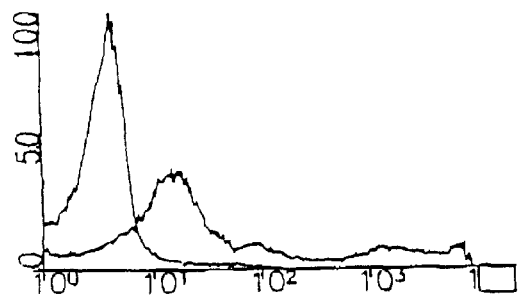
Figure 2D:
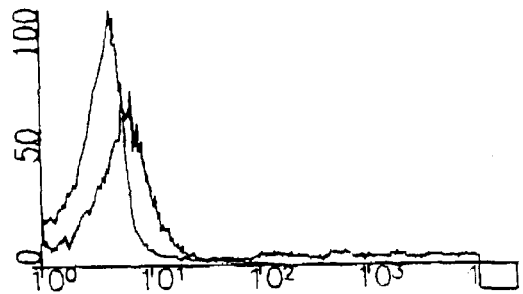
Figure 2E:
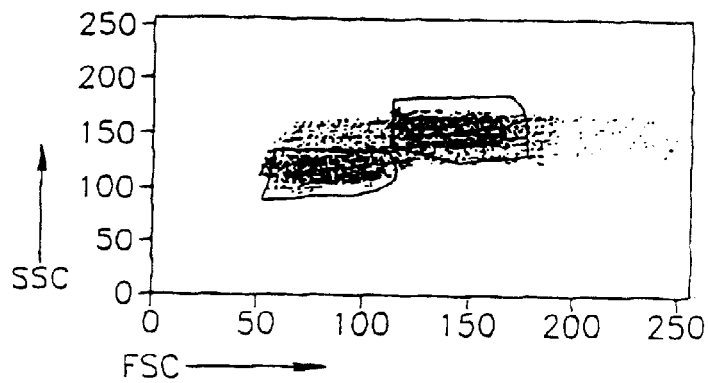
Figure 2F:
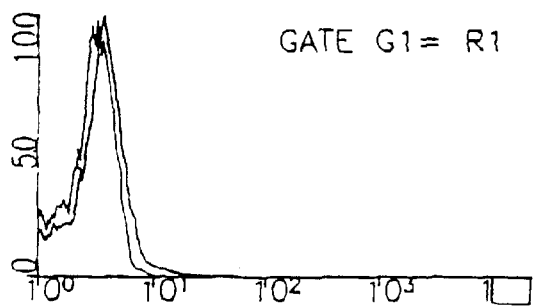
Figure 2G:
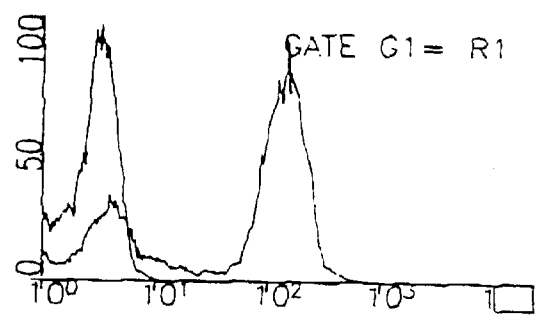
Figure 2H:
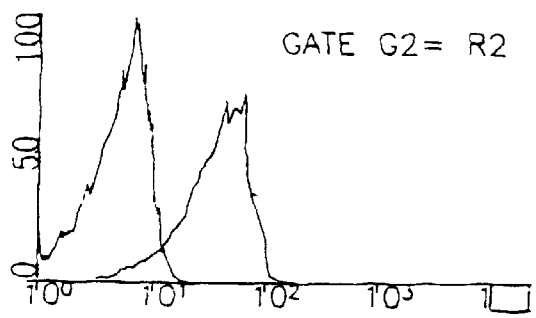
Figure 2I:
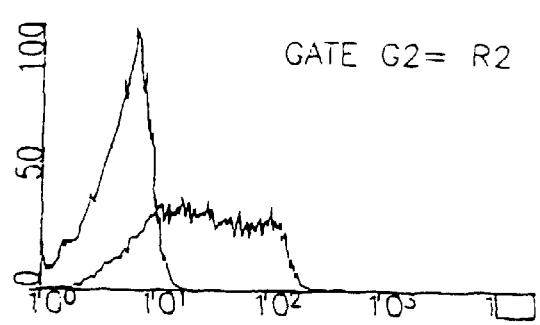
Figure 3A:
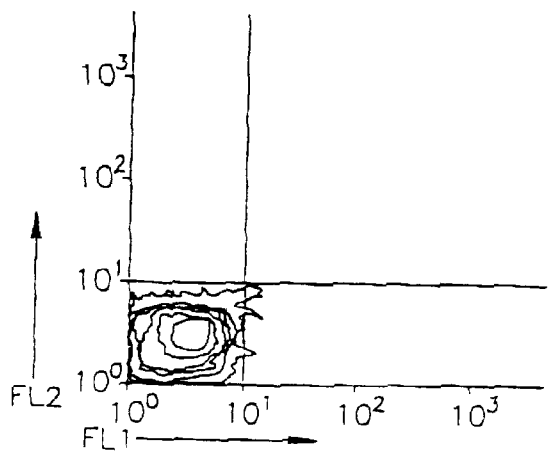
Figure 3B:
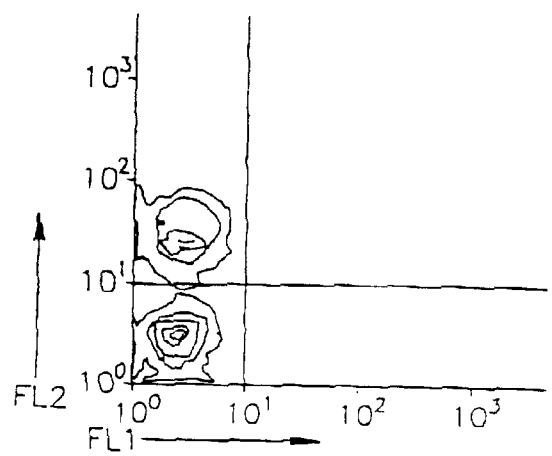
Figure 3C:
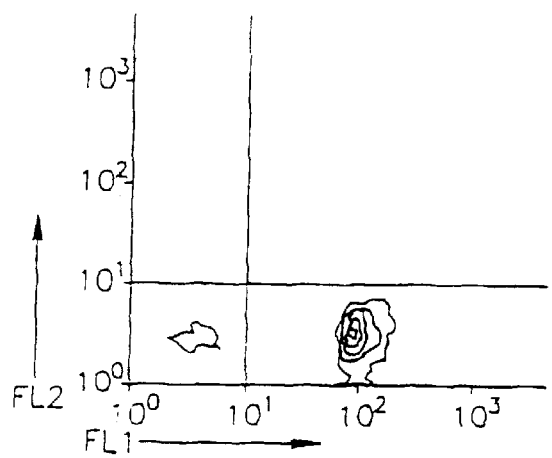
Figure 3D:
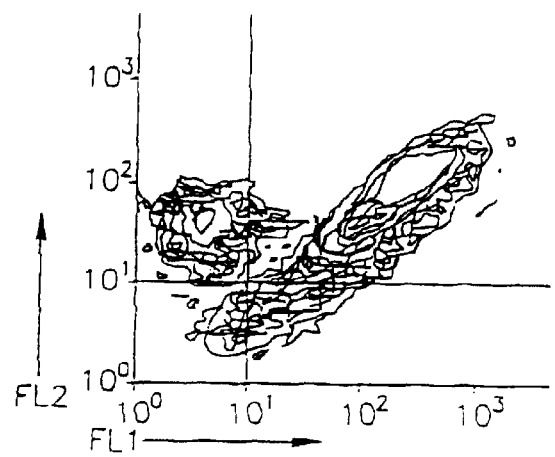

BALB/c mice were immunized with membrane preparation of Daudi cells. Membranes from Daudi cells were prepared by the glycerol load-hypotonic shock method (Jett, M., Seed, T. M., and Jamieson, G. A., *J. Biol. Chem.*, 252:2134, (1977)). 50–80×10$^6$ cells suspended in PBS and incubated at 37° C. were gradually loaded with 30% glycerol. After 5 mins. incubation on ice, they were centrifuged and resuspended in cold Tris lysate buffer (containing 10 mM Tris-HCl, 1 mM $MgCl_2$, 1 mM $CaCl_2$, pH 7.4) mixed for 5 mins. at 4° C. and centrifuged at 700 g. Supernatants were removed and centrifuged at 3300 g (10 mins. 4° C.). The pellet was washed again and the two supernatants containing membrane fraction were pooled. 260 µl of membrane preparation (3 mg/ml) were emulsified with 260 µl of complete Freund adjuvant and injected i.p. into BALB/c mice. Three weeks later the spleens of mice were removed. Splenocytes were fused with the myeloma cell line NS-O at a ratio of 10:1. Fusion was performed using polyethylene glycol and the hybridomas were grown in selective media according to Kohler and Milstein (Kohler, G., and Milstein, C., *Nature,* (London) 256:495, (1975)).

A cell bound enzyme linked immmunosorbent assay (ELISA) was used to screen supernatants from growing hybridomas (Glassy, M. C. and Surh, C. D., *J. Immunol. Method,* 81:115 (1985)) which bind to Daudi cells. Positive hybridoma supernatants were then further selected by their ability to induce proliferation of human PBM using [$^3$H] Thymidine uptake assay. Positive clones were subcloned by limited dilution, repeatedly tested, expanded and grown in culture.

mAbs were purified from culture medium by 50% ammonium sulfate precipitation, followed by extensive dialysis against PBS. Further purification was performed by affinity chromatography on sepharose bound anti-mouse antibody columns.

Culture Medium

All cells were suspended in RPMI 1640 medium supplemented with 10% fetal calf serum (FCS), Na-pyruvate (1.1 mg/ml), L-glutamine (0.3 mg/ml) and antibiotics (Penicillin 200 u/ml and streptomycin 10 µg/ml) and incubated in 5% $CO_2$ humid incubator.

IL-2 units used are Cetus units (1 Cetus unit equals 3 International units).

Cell Preparations

Human peripheral blood mononuclear cells (PBM) were obtained from healthy adult donors by ficoll-hypaque density centrifugation (Histopaque, Sigma). PBM were depleted of monocytes by sephadex G10 columns. T cells were separated by SRBC rosetting method. Depletion of CD3 positive and Leu19 positive cells was performed by immunomagnetic technique. Cultures of PBM incubated for 5–6 days with BAT mAbs or control were washed three times with PBS. Unconjugated antibodies to either CD3 or Leu19 (CD56) were added to the cells in complete RPMI medium and incubated for one hour at 4° C. Magnetic beads coated with antimouse antibody were added for 30 mins. The cells attached to the beads were removed with the magnet and the unattached cells were analyzed for cytotoxic activity and stained by flow cytometry.

Cytotoxicity Assay

Cytotoxicity assays were done as follows: 2–4×10$^6$ target cells were mixed with 200 µCi of $^{51}$Cr-chromate for 1 hour in serum free medium. They were washed three times with complete medium and finally resuspended in RPMI-10% FCS and plated at 10$^4$ cells per well. Effector cells were cultured, lymphocytes prepared from normal peripheral blood incubated for various time periods with the different mAbs, isotypic control IgG or with IL-2. Prior to the assay the cells were washed three times in RPMI medium, stained for viability cells using 1% Trypan blue, mixed with target cells at various effector-target ratios in round bottom microtiter plates and incubated for 3 hours at 37° C. in a 5% $CO_2$. The culture supernatants were harvested and counted in a β-scintillation counter. Maximum isotope release (MR) is produced by incubation of the target cells with triton x-100. Spontaneous release (SR) is measured by incubation of the targets with medium alone. Percentage of cell lysis is calculated by (ER-SR/MR-SR)×100, where ER is the experimental effector release.

Induction of Cytotoxicity in Human Lymphocyte Subpopulations

PBM cells (4.10$^6$/ml) were cultured for 6 days in the presence of BAT mAbs. Thereafter the cells were washed three times and were depleted of CD3 and Leu19 cells by magnetic beads coated with anti-mouse f(ab')$^2$ and tested for cytotoxicity against K562 and Daudi cells.

Flow Cytometry

Cell surface antigens were detected by flow cytometry using a FACS 440 (Becton-Dickinson). For each analysis 10$^6$ cells were used. The cells were stained by sequential incubation with all optimal concentration of murine mAb to human CD3, IL-2 receptor, or the mAb BAT 1–9 that were produced. FITC-conjugated goat anti-mouse F(ab')$_2$ was used as a second antibody in this indirect straining. Each incubation was carried in PBS pH 7.4 containing 1% BSA and 0.5% Na-azide for 30 mins. at 4° C. and was followed by three washings with the same buffer. 10$^4$ stained cells were analyzed.

Detection of BAT mAb Binding Determinant(s)

Detection of BAT mAb binding determinant(s) on Daudi B lymphoblastoid cell lysates, was done using Western Blot technique. Briefly, 50×10$^6$ cells/ml suspended in PBS was gradually loaded with 30% glycerol and membranes were separated by sequential centrifugations.

Samples of the membrane preparations were separated by SDS-PAGE (12%) and then transferred to nitrocellulose blots which were immersed in 1% low fat milk in PBS. Detection of the BAT mAb binding protein in the nitrocellulose blots was done by incubating the blots with BAT mAb for 2 hours at room temperature, followed by 30 mins. incubation with peroxidase-horseradish-conjugated antibody 70 anti-mouse IgG (Fab')$_2$. The cells were then rinsed and bands were detected with O-dianizidine substrate.

Mouse Tumor Models

Three mouse tumor models were used: B16 melanoma, Lewis lung carcinoma (3LL) and methylcholanthrene induced fibrosarcoma (MCA 105). 50–200×10$^6$ cells were injected i.v. to C57BL mice (8 weeks of age). Two weeks later, BAT-1 was injected (i.v.), 1–10 µg/mouse and 10 days later mice were sacrificed and established lung metastases were counted.

EXAMPLES

EXAMPLE 1 a. Binding Characteristics

Nine monoclonal antibodies (mAbs) designated BAT 1–9, obtained by immunization with B lymphoblastoid cells, were selected first for binding to Daudi cells and then for inducing human peripheral blood lymphocytes proliferation. The isotypes of BAT mAbs were determined by both ELISA and Ochterlony assays. BAT 1,2,3,6,7 and 9 were found to be of IgG1 class whereas BAT 4 and 5 were of the IgM class. BAT 8 was IgG2a.

Binding of the above Mabs to purified peripheral human T cells was analyzed by FACS analysis using indirect immunofluorescence staining. FIG. 1A–1F demonstrates FACS analysis of such an experiment. As can be seen, BAT mAbs bind to peripheral blood CD3+ T cells. The extent of binding varied from BAT-2 44% BAT-5 38%, BAT-1 32% to a somewhat weaker binding of BAT-4 (13%). Purified peripheral blood B lymphocytes from the same blood donors, did not bind these mAbs (data not shown).

b. Binding of BAT-1 mAb to Human Lymphocyte Subpopulations

As seen in FIG. 2A–2I, further FACS analysis showed that BAT-1 binds CD3+ human PBM as well as cells of the Jurkat T-cell line. The finding that BAT-1 binds to CD3+ PBM cells was even further corroborated using FACS analysis of double labeled cells (FIG. 3A–3G).

As seen in Table 1 below, BAT-1, in addition to its binding to CD3 bearing cells, binds also to Leu 19/NK cells.

TABLE 1

Binding of BAT-1 mAb to human lymphoid subpopulations

| | Positive cell (%) Subpopulation of cells enriched for | |
|---|---|---|
| mAb | CD3+ | Leu 19+ |
| CD3 | 66.4 (100%) | — |
| Leu 19 | — | 59.5 (100%) |
| BAT-1 | 19.8 (30%) | 42.2 (70%) | c. Binding of BAT mAbs to Various Cell Types

Binding of BAT mAbs to various cell types was determined. As can be seen in Table 2 below, BAT mAbs bind to K562, an erythroleukemia cell line, and MCF7, a human mammary carcinoma cell line, in addition to their binding to PBL, Daudi and the Jurkat T cell line. The extent of binding varied among the BAT mAbs and cell types tested. mAbs 2–9 bound to the mouse renal carcinoma (MR28) only with very low affinity. Only BAT-8 bound to MEL (murine erythroleukemia) cells, also at a very low affinity.

TABLE 2

Binding of BAT mAbs to various cell types

| | BAT mAb | | | | | |
|---|---|---|---|---|---|---|
| Cells | 1 | 2 | 4 | 5 | 8 | 9 |
| Human | | | | | | |
| Daudi | +++ | ++ | ++ | +++ | ± | +++ |
| Jurkat | + | ± | +++ | +++ | − | +++ |
| PBL | +++ | ± | + | + | ± | ± |
| K562 | +++ | + | + | +++ | ± | +++ |
| MCF7 | ± | ++ | +++ | +++ | + | +++ |
| Mouse | | | | | | |
| MR28 | − | ± | + | + | ± | ± |
| MEL | − | − | − | − | ± | − |

Binding was assayed by ELISA and is expressed as:
+ (0.1–0.2 OD)
++ (0.2–0.3 OD)
+++ (over 0.3 OD)

EXAMPLE 2

Analysis of BAT mAb Binding Site and Purification of the BAT-1 Binding Protein

Figure 4:
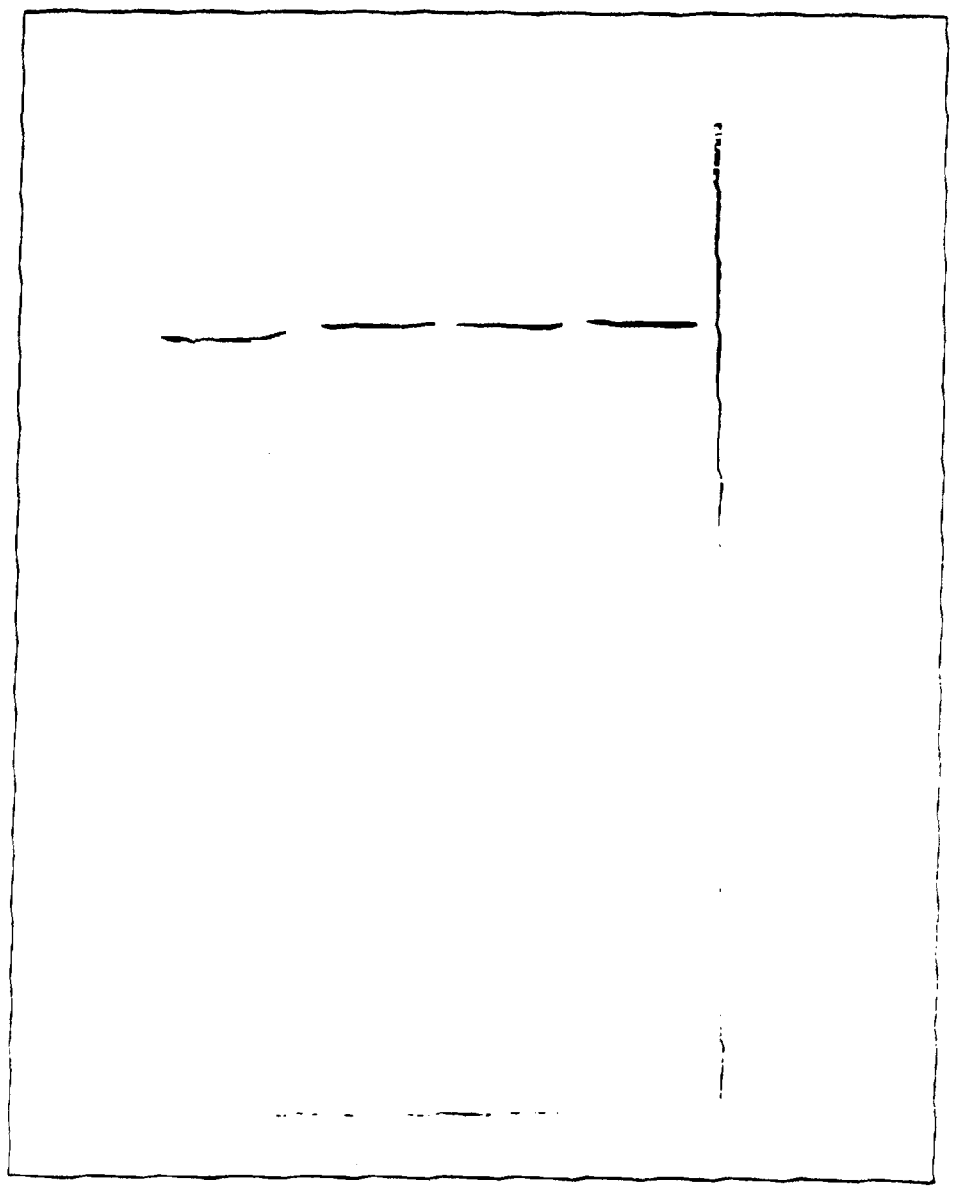
FIG. 4 shows Western Blot analysis of the binding of BAT-1 antibodies to different lysates of Daudi cells.

In order to determine the molecular weight of the membrane protein that interacts with the BAT-1 mAbs, a membrane preparation of Daudi cells was solubilized and the protein was separated by SDS-PAGE. Nitrocellulose transferred blots were incubated with BAT-1 mAb and bands were detected by further incubation with horseradish-peroxidase-conjugated antibody to anti-mouse IgG $(Fab')_2$ and detection using O-dianizidine substrate. The molecular size of the BAT-1 binding protein was found to be about 48–50 KDa (FIG. 4).

The BAT mAb binding protein was purified using BAT mAb conjugated to Sepharose. This binding protein can also be prepared by cloning using molecular biology techniques. Administration of BAT-1 in vivo to mice results in the induction of BAT antibodies.

EXAMPLE 3

Functional Characteristic of BAT mAbs a. BAT mAbs Induced Thymidine Incorporation Human peripheral blood cells were cultured for 6 days in the presence of increasing concentrations of a panel of BAT mAbs and pulsed with [$^3$H]Thymidine 20 hours prior to harvesting.

Figure 5:
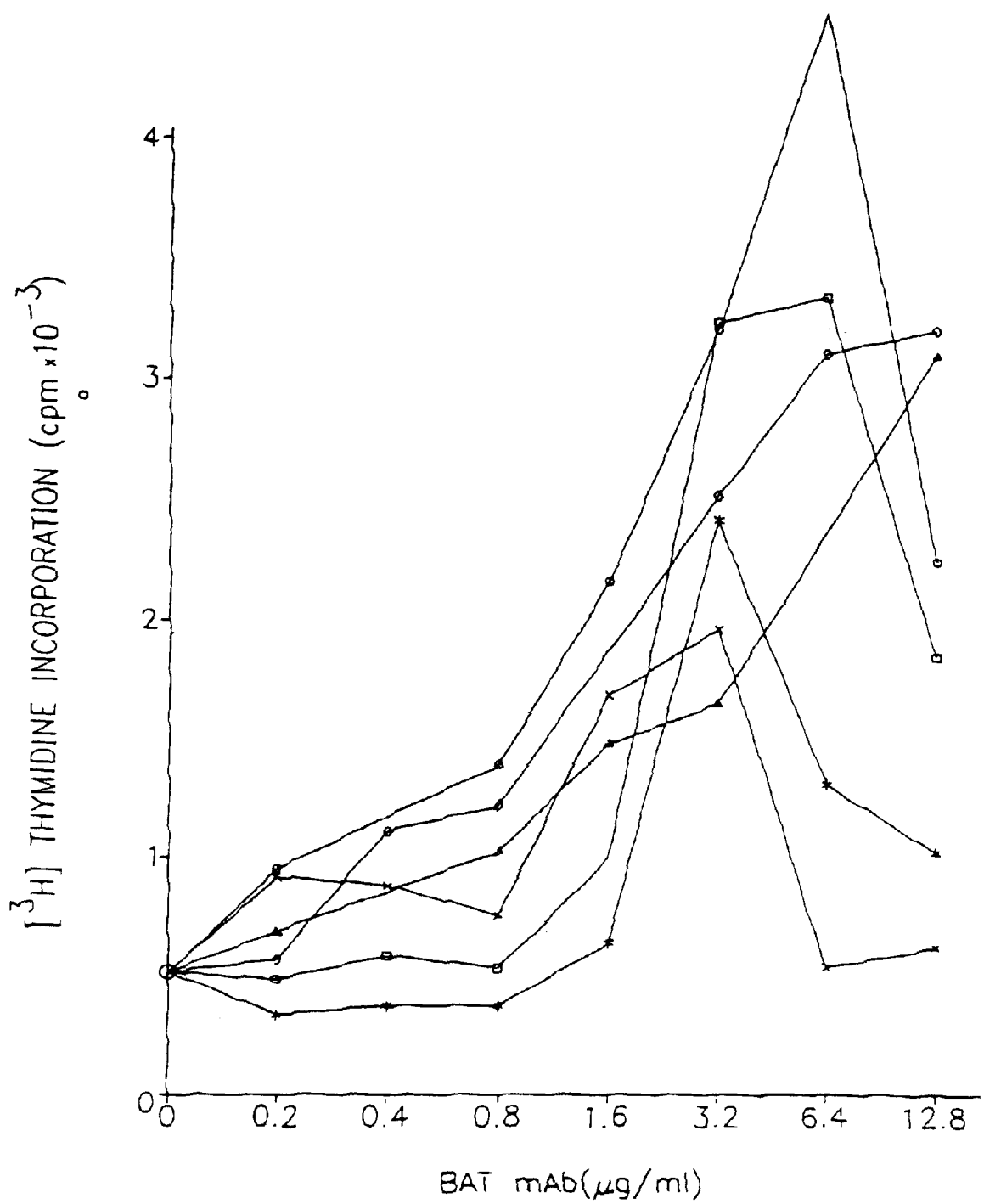
FIG. 5 is a graphical representation of results of [$^3$H] Thymidine incorporation in cells cultured for six days in the presence of increasing concentrations of a panel of BAT Mabs: BAT-1 (—▲—), BAT-2 (—X—), BAT-3 (—●—), BAT-5 (—★—), BAT-6 (—♦—), BAT-7 (—■—).

As seen in FIG. 5, a gradual increase in concentrations of BAT mAbs resulted in a modest but significant increase in [$^3$H]Thymidine incorporation in the PBM cells. However, a high dose of antibody caused a decrease in uptake by the cells. In control experiments, isotype matched antibodies did not increase the [$^3$H]Thymidine in PBL cells indicating that the agonistic effect of the BAT mAbs was dependent on their binding specific properties. For example, mAb of the IgG1 isotype, that was raised in our laboratory against ovarian carcinoma cells, caused no increase in [$^3$H]Thymidine uptake in contrast to BAT 1,2,3,6,7 and 9 mAbs which also belong to the IgG1 class.

b. BAT mAbs Induce Cytotoxicity in Human PBM

Cultures of human peripheral blood mononuclear cells incubated with BAT mAbs for various time periods, were tested for their ability to lyse tumor cell lines.

As seen in Table 3 below, human PBM cells incubated for one week with a panel of BAT mAbs wore cytotoxic against K562, human erythroleukemia (NK sensitive) and RC-29, renal carcinoma cell line (NK resistant) cells.

Figure 6A:
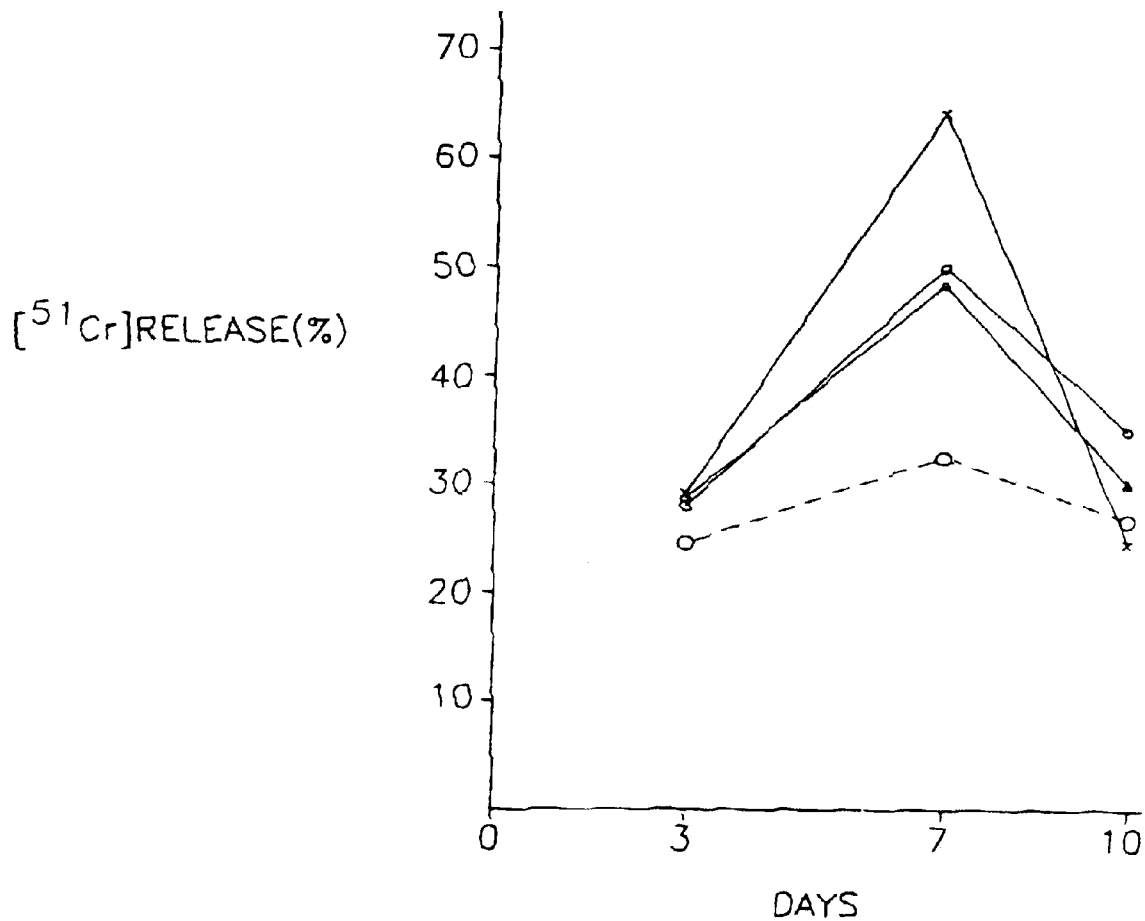
FIG. 6 is a graphical representation of an experiment in which the induction of cytotoxic activity was tested in PBM cultured for various time intervals with 2.5 μg/ml BAT mAbs. HT-29 (left) or RC 29 (right) cells were used as target cells. Effector to target ratio was 20:1. Control (—O—, BAT-1 (—●—), BAT-2 (—X—) BAT-3 (—▲—).
Figure 6B:
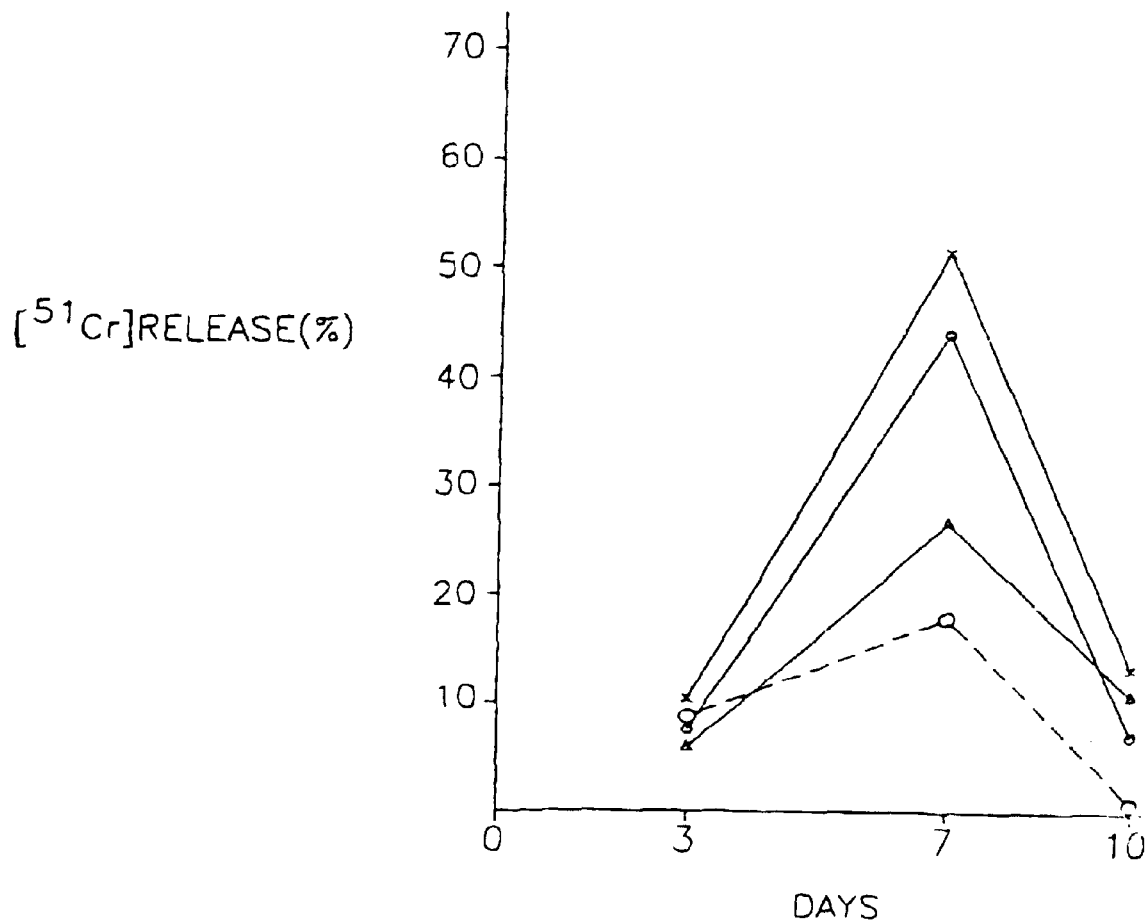

The kinetics of the increase in cytotoxic activity of human PBM that were stimulated with BAT mAbs was investigated. As seen in FIG. 6, maximal cytotoxicity toward human colon carcinoma (HT-29) and renal cell carcinoma (RC-29) was attained after 7 day incubation of human PBM with BAT mAbs.

TABLE 3

BAT mAbs induce cytotoxicity in human PBM

| | Specific $^{51}$Cr release (%) | |
|---|---|---|
| mAb | K562 | RC-29 |
| None | 11.0‡ | 9.1 |
| BAT-1 | 25.1 | 45.4 |
| 2 | 29.0 | 23.2 |
| 3 | 26.3 | 32.3 |
| 4 | 30.6 | 40.7 |
| 5 | 32.3 | 34.3 |
| 6 | 15.2 | 13.8 |
| 7 | 17.8 | 16.7 |
| 8 | 17.8 | 19.2 |
| IL2 1000 u/ml | 57.6 | 36.9 |

‡Percent lysis of target cells using effector: target ratio of 5:1 c. Characterization of Lymphocyte Subpopulation Involved in BAT-Induced Cytotoxicity In order to assess whether the increase in cytotoxic activity of human PBM induced by BAT mAbs, is due to activation of NK cells, T cells or both, NK and T cells were purified and their cytotoxicity induced by BAT was determined. For purification of the NK and T cells Leu19 and anti CD3 monoclonal antibodies were incubated with the human PBM cells, followed by incubation with anti-mouse IgG coated magnetic beads. This led to depletion of the subpopulations of cells which bind to the corresponding antibody. As can be seen in Table 4 below, the number of lytic units increased in both the CD3 depleted and Leu19 depleted cell cultures. BAT 6 and 8 were used in these experiments and the targets were human erythroleukemia (K562) and human lymphoma (Daudi).

TABLE 4

BAT mAbs induct cytotoxicity in human lymphocyte subpopulations

| | Lytic Units Target cells | | | |
|---|---|---|---|---|
| | K562 | | Daudi | |
| | effector cells depleted of | | | |
| | CD3 | Leu 19 | CD3 | Leu 19 |
| Control | 8 | 4 | 10 | 3.8 |
| BAT 6 | 25 | 10 | 20 | 13 |
| BAT 8 | 28 | 12.5 | 26 | 20 |

EXAMPLE 4
Synergism Between BAT mAb and IL-2 in the Induction of Cytotoxicity

Induction of cytotoxicity in human PBM was studied upon incubation of the PBM cells with BAT mAb in combination with IL-2. IL-2 at suboptimal concentrations (1 U/ml) was added together with increasing concentrations of BAT-2 mAb. Cytotoxicity was tested after one week in culture against K562 and HT19 tumor cell lines. As shown in Table 5 below, low concentration of BAT-2 synergized with IL-2 in the induction of cytotoxicity of the PBM cells against both kinds of target cells.

INF-α was previously shown to enhance the expression of MHC-I class antigens. Therefore, administration of INF-α is likely to potentiate the anti-tumor effect of BAT which is mediated by cytotoxic cells directed against various tumor cells (Bearing MHC class I antigens).

TABLE 5

Synergistic effect of BAT-2 mAb and IL2 in the induction of cytotoxicity in human PBL

| | Specific$^{51}$ Cr release (%) Target cells | | | |
|---|---|---|---|---|
| | HT29 | | K562 | |
| BAT | IL-2 (1 U/ml) | | | |
| (μg/ml) | − | + | − | + |
| 0 | 5.8 ± 0.1 | 7.5 ± 0.3 | 3.7 ± 0.1 | 6.9 ± 0.4 |
| 2 | 14.8 ± 1.3 | 37.6 ± 2.0 | 12.1 ± 0.4 | 29.6 ± 1.6 |
| 4 | 16.7 ± 0.6 | 27.3 ± 1.0 | 13.3 ± 0.6 | 18.5 ± 1.2 |
| 8 | 22.0 ± 1.0 | 15.1 ± 0.6 | 19.9 ± 0.7 | 12.5 ± 0.4 |

EXAMPLE 5
Immune Stimulatory Effects of BAT-1 Mice
a. In Vitro Studies

The mAb BAT-1 demonstrates stimulatory properties in murine splenocytes similar to those seen in human PBL. They include:
(i) Increased splenocyte proliferation in vitro as measured by $^3$HThymidine incorporation (Table 6);
(ii) Synergistic stimulatory effect by incubation of splenocytes with a combination of BAT-1 and IL-2 (Table 6);

TABLE 6

| BAT-1 | cpm [$^3$H] Thmidine × 10 IL2 | | |
|---|---|---|---|
| (μg/ml) | − | 1 U/ml | 10 u/ml |
| − | 1.5 ± 0.07 | 16.0 ± 0.9 | 67.5 ± 1.6 |
| 10 | 11.0 ± 0.4 | 32.1 ± 1.5 | 241.6 ± 17.1 |
| 1 | 12.9 ± 0.8 | 35.9 ± 3.3 | 247.8 ± 1.9 |
| 0.1 | 18.1 ± 0.9 | 51.0 ± 7.3 | 255.1 ± 18.0 |
| 0.001 | 10.5 ± 0.1 | 34.1 ± 0.5 | 215.1 ± 20.8 |
| 0.0001 | 2.6 ± 0.1 | 13.2 ± 0.9 | 73.3 ± 5.6 |

C57BL murine splenocytes incubated for 5 days in vitro with various concentrations of BAT-1 and in combination with interleukin-2 (1 u and 10 u per ml).

(iii) Increased cytotoxicity in murine splenocytes cultures in the presence of BAT-1 and further increase in cytotoxicity upon incubation in the presence of IL-2 (Table 7).

TABLE 7

| BAT-1 | Specific$^{51}$ Cr release (%)$^2$ Interleukin-2 | | |
|---|---|---|---|
| (ng/ml) | − | 1 u/ml | 10 u/ml |
| − | 7.4 | 10.0 | 31.1 |
| 100 | 24.9 | 31.3 | 52.4 |
| 10 | 17.4 | 26.7 | 52.8 |
| 1 | 12.3 | 23.9 | 46.8 |
| 0.1 | 12.2 | 21.7 | 45.5 |

Induction of cytotoxicity in C57BL splenocytes cultures for 5 days in vitro in the presence of various BAT-1 concentrations and in combinations with low does IL-2.
$^2$B16 melanoma cells were used as a target. Effector to target cell ratio was 50:1

Murine tumor target cells that were susceptible to the killing effect by BAT-1 activated splenocytes included: B16 melanoma, Lewis lung carcinoma (3LL), fibrosarcoma (MCA 105), renal cell carcinoma (MR 28) and lymphoma (YAC) (Table 8).

TABLE 8

BAT-1 induced cytotoxicity in splenocytes against mouse tumor cells (In in vitro study)

| | | Specific$^{51}$ Cr release %$^2$ BAT-1 | |
|---|---|---|---|
| Mouse strain | Tumor target cells | − | + |
| C57BL | B16 melanoma | 5.4 | 13.6 |
| | Lewis lung carcinoma (3LL) | 11.2 | 24.0 |
| | Fibrosarcoma (MCA 105) | 27.0 | 45.0 |
| BALB/C | Lymphoma (YAC) | 8 | 12.2 |
| | Renal cell carcinoma (MR28) | 0.1 | 5.2 |

$^2$Splenocytes were cultured, in vitro, for 5 days, in the absence of BAT-1 mAb (1 μg/ml).
Cytotoxicity was determined at an effector/target ratio of 60:1.

b. In Vivo Studies

As seen in Table 9 below, BAT-1 manifested immune-stimulatory effects upon administration in vivo. They included:
(i) Stimulation of [$^3$H]Thymidine incorporation in splenocytes from mice injected 10 days earlier with BAT-1 (Table 9A). Maximal stimulation (10 fold) was attained upon administration of BAT at doses of 10 μg/mouse.

(ii) Induction of cytotoxicity in splenocytes from mice injected with BAT-1 (Table 9B). BAT-1 administered at different doses 10 days prior to the cytotoxicity assay induced cytotoxicity towards murine melanoma (B16-F10) cells, renal cell carcinoma (MR-28) cells and lymphoma (YAC) cells. Maximal effect was attained upon administration of BAT at a dose of 10 µg/mouse.

TABLE 9

Proliferation and cytotoxicity of splenocytes from mice injected with BAT mAb

| A [$^3$H] Thymidine incorporation | BAT | B Specific$^{51}$ Cr release (% ± SEM) Cell Target | | |
|---|---|---|---|---|
| cpm 10 ± SEM | (µg/mouse) | B16 | MR-28 | YAC |
| 9.9 ± 1.5 (n = 16) | 0 | 3.9 ± 1.4 (n = 10) | 16.0 ± 2.7 (n = 8) | 3.3 ± 0.4 (n = 6) |
| 15.3 ± 2.3 (n = 12) p < 0.1 | 1 | 13.2 ± 1.4 (n = 6) p < 0.001 | 31.7 ± 2.8 (n = 8) p < 0.01 | 16.7 ± 1.6 (n = 6) p < 0.001 |
| 20.0 ± 4.0 (n = 14) p < 0.05 | 10 | 14.0 ± 1.2 (n = 6) p < 0.001 | 25.2 ± 2.1 (n = 8) p < 0.02 | 19.0 ± 2.6 (n = 6) p < 0.001 |

Mice C57BL and BALB/c were inject I.V. with BAT mAb at different concentrations. 10 days later cytotoxity and [$^3$H] Thymidine incorporation was determined in isolated splenocytes. Splenocytes from C57BL mice were tested on B16 melanoma target cells and from BALB/c mice were tested on MR-29 and YAC cells (effector: target ration 50:1). Each group contained beteeen 6–16 mice in 3–4 separate experiments. Cytotoxicity and [$^3$H] Thymidine incorporation for eachmouse was done in triplicates and the mean calculated. results are expressed at mean ± standard error of n mice, p-values for the differences between the control and the BAT treated animals are given.

EXAMPLE 6
Immunotherapeutic Effect of BAT-1 Against Mouse Tumors

As seen in Table 10, administration of BAT-1 to melanoma-inoculated mice 14 days after inoculation of the tumor cells, reduced the number of lung metastases in lungs of mice bearing B16, 3LL and MCA tumors:

a1. BAT-1 Abolishes Lung Metastases in B16 Melanoma-Inoculated Mice, Using an Established Lung Metastases Model C57BL mice were injected (i.v.) with 50×10$^3$ B16 melanoma cells (Table 10). 24 days after injection numerous metastases developed in the lungs (practically reached confluency) as seen in FIG. 7, upper row.

Figure 7:
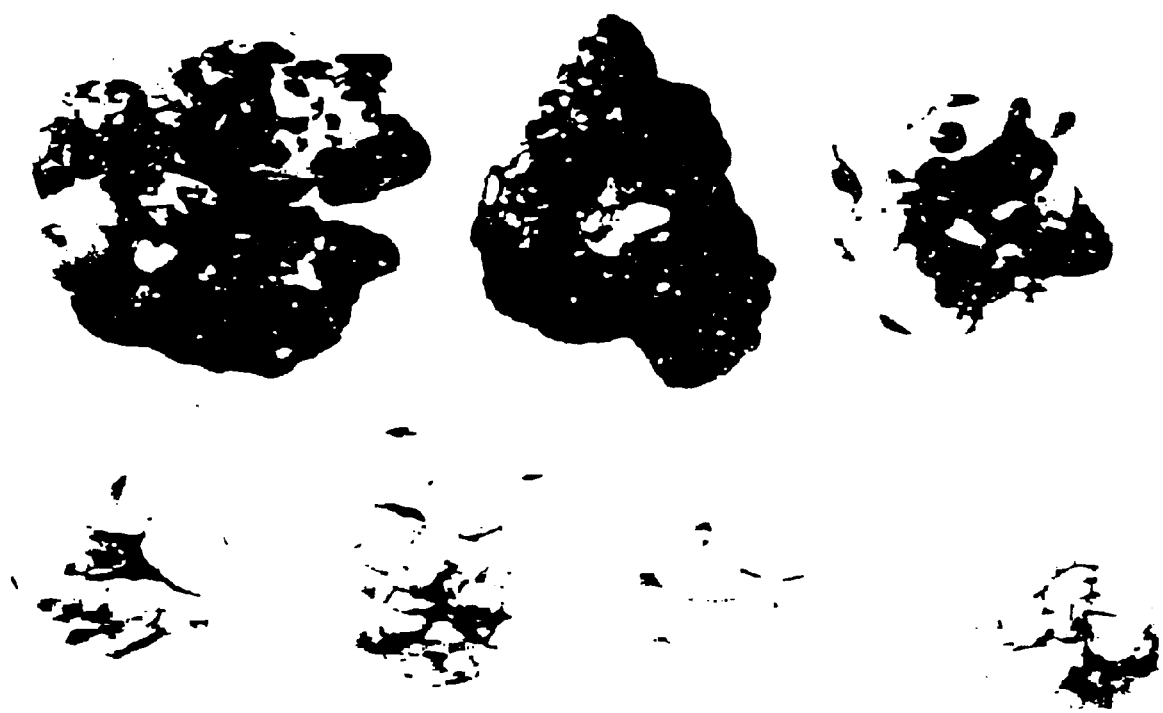
FIG. 7 shows lungs from C57BL mice inoculated with B-16 melanoma cells: Upper row shows lungs of mice inoculated with cells only, 24 days after inoculation; lower row shows lungs of mice inoculated with B-16 cells as above followed 14 days later by I.V. injection of 10 μg f BAT-1 mAbs, 24 days after inoculation.

Against this, as seen in FIG. 7, lower row, lung of mice that were injected with BAT-1 (10 µg/mouse) two weeks after inoculation with the B16 melanoma were practically free of metastases.

Figure 8:
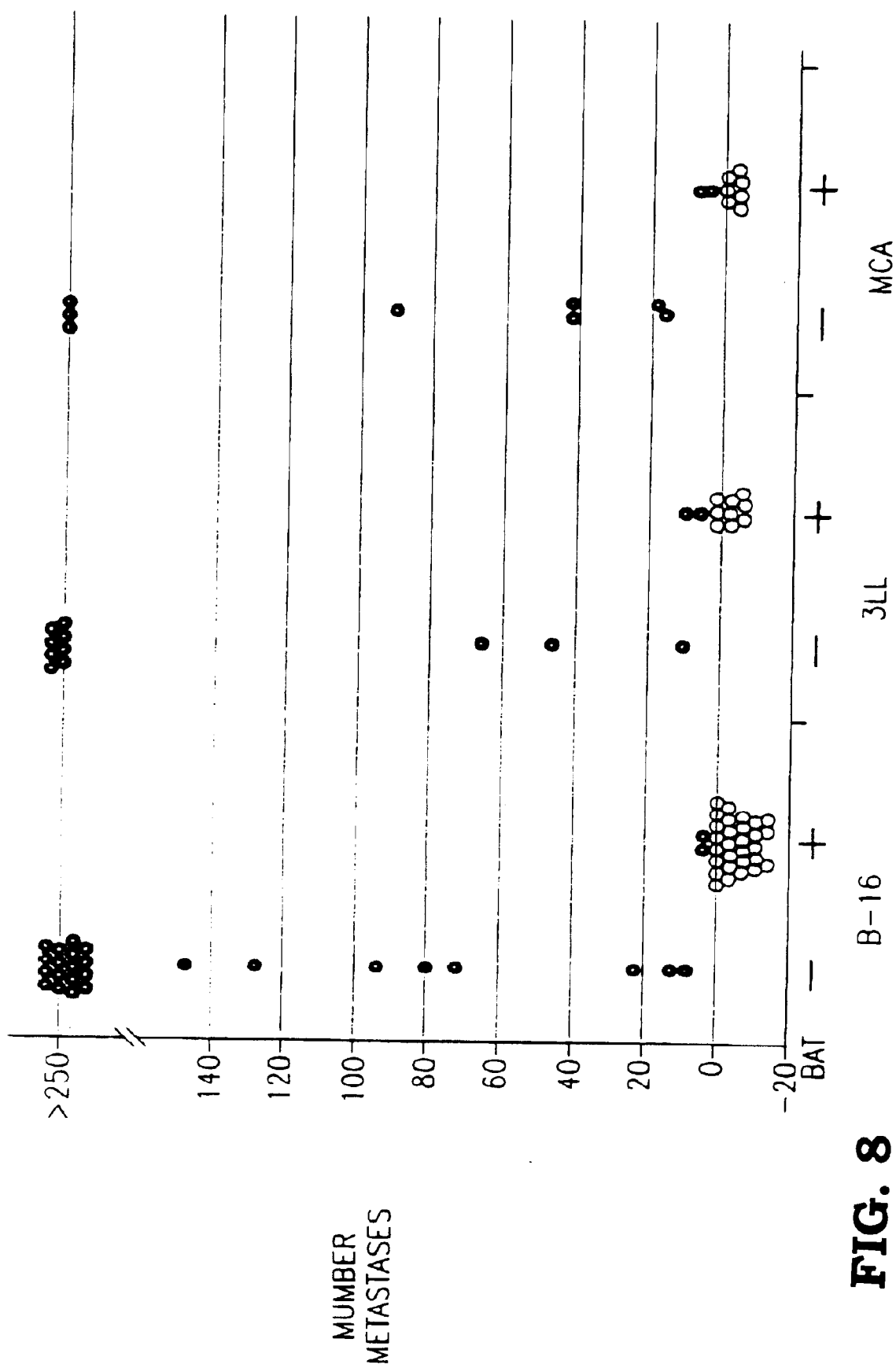
FIG. 8 is a graphical representation of a summary of experiments of the kind shown in FIG. 7, showing the number of metastasis in lungs of mice which were inoculated with tumor cells being either B-16 melanoma cells, 3LL Lewis lung carcinoma cells or MCA 105 fibrosarcoma cells, one month after inoculation. The results summarize 3–4 experiments carried out with each kind of tumor. Mice untreated (−) or treated (+) with BAT-1 (10 μg/mouse) 2 weeks after tumor administration. Metastasis (●); no metastasis (○).

FIG. 8 summarizes the results of six separate experiments done under similar conditions as above.

TABLE 10

Anti tumor effect of BAT mAB
BAT-induced reduction in lung metastases

| | Tumors$^a$ | | | | | |
|---|---|---|---|---|---|---|
| | B16 | | 3LL | | MCA | |
| | BAT treatment$^b$ | | | | | |
| No. of mets.$^c$ | − (n = 24)$^d$ | + (n = 27) | − (n = 11) | + (n = 11) | − (n = 8) | + (n = 9) |
| None | 0 | 25 | 0 | 6 | 0 | 4 |
| 1–10 | 0 | 2 | 0 | 4 | 0 | 5 |
| 11–50 | 8 | 0 | 3 | 1 | 5 | 0 |
| >250 | 16 | 0 | 8 | 0 | 3 | 0 |
| Lung weight (gr) | 0.803$^e$ ± 0.26 | 0.315 ± 0.66 | 1.014 ± 0.21 | 0.364 ± 0.06 | 0.836 ± 0.31 | 0.328 ± 0.06 |

$^a$Tumor was inoculated at day 0
$^b$BAT mAb (10 µg/mouse) was injected i.v. at day fourteen
$^c$Lung metastases were scored 24 days post tumor inoculation using a Zeiss stereomicroscope
$^d$Number of mice
$^e$Mean ± SD of lungs weight from (n) mice a2. Anti-Tumor Effect of BAT-1 mAb Injected at Different Times in Relation to B16 Tumo Inoculation As seen in Table 11, mice given injections of the melanoma cells and treated 10–14 days later by BAT-1 mAb administration were found to be free of metastases and have normal lung weights. A marked decrease in the number of metastases in the lungs of the mice, although not complete, was noticed 5 days after tumor inoculation and as late as 19 days post-tumor administration. Injection of BAT-1 on the same day as inoculation of tumor cells had no thereapeutic effect.

TABLE 11

BAT administration at different times in relation to B16 melanoma inoculation

| Day | No. of Mice | No. of Mets. | lungs weight (gr) |
|---|---|---|---|
| None | 10 | 155.0 ± 28 | 0.892 ± 0.19 |
| −6 | 3 | 61.0 ± 0.8 | 0.983 ± .01 |
| 0 | 7 | 148.0 ± 36 | 0.425 ± 0.05 |
| 5 | 4 | 0.8 ± 0.5 | 0.243 ± 0.07 |
| 10 | 4 | 0.0 ± 0.0 | 0.240 ± 0.08 |
| 14 | 7 | 0.0 ± 0.0 | 0.286 ± 0.03 |
| 19 | 4 | 2.2 ± 1.3 | 0.338 ± 0.01 |
| 23 | 4 | 75.4 ± 44 | 0.840 ± 0.24 |

Figure 9:
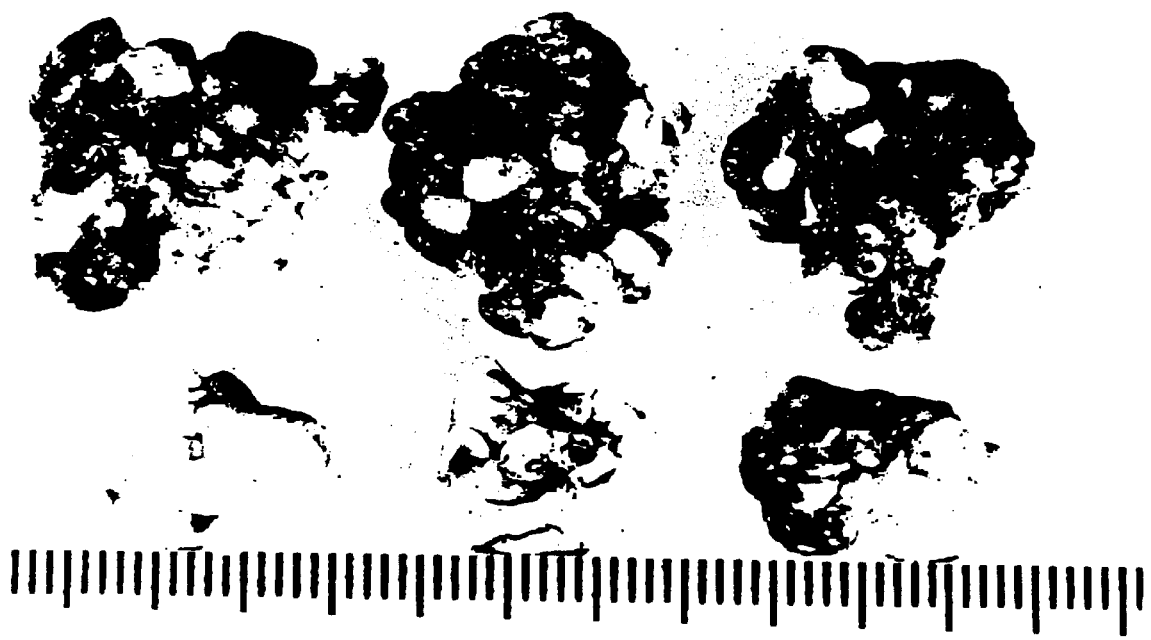
FIG. 9 shows lungs from mice inoculated with 3LL Lewis lung carcinoma cells. Similarly as in FIG. 7, the upper row shows lung inoculated with tumor cells only and the lower row shows lungs of mice inoculated I.V. 14 days later with 10 μg of BAT-1 mAbs.
Figure 10:
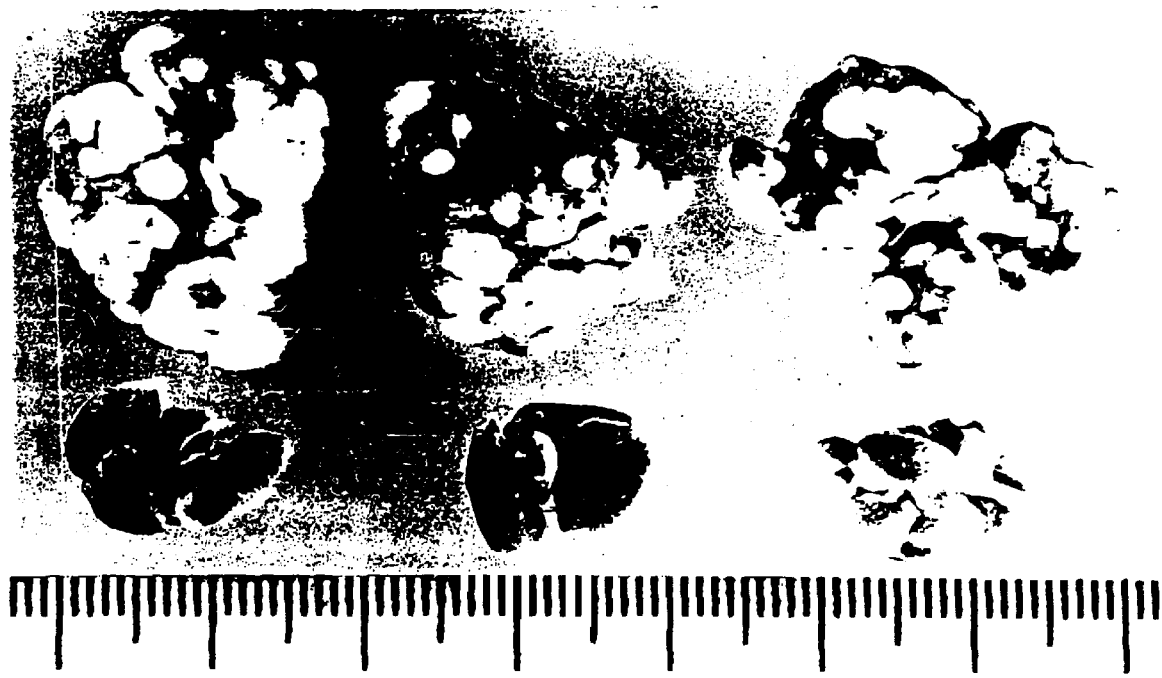
FIG. 10 shows a similar experiment as that shown in FIG. 9 where the tumor cells are MCA 105 fibroblastoma cells.

$^f$Day of BAT mAb admimistration relative to tumor inoculation at day zero.

b. BAT-1 Abolishes Lung Metastases in Lewis Lung Carcinoma (3LL)-Inoculated Mice Using an Established Lung Metastases Model Experimental conditions were similar to those described for B16 melanoma (see above) except that 2×10$^5$ 3LL cells were injected. FIG. 9, upper row, shows lungs from 3LL-inoculated mice with numerous metastases. FIG. 9, lower row shows lungs from mice that had been inoculated with the tumor cells followed 14 days later by BAT-1 treatment which as seen, are almost free of metastasis.

c. BAT Abolishes Lung Metastases in MCA Fibrosarcoma (MCA 105)-Inoculated Mice Using an Established Lung Metastases Model Experimental conditions were similar to those described for the 3LL Lewis lung carcinoma model. FIG. 10, upper row, shows lungs from MCA 105 inoculated mice with numerous metastases. FIG. 10, lower row shows lungs from mice that had been inoculated with the tumor followed by BAT-1 treatment which, as seen, are almost free of metastases.

EXAMPLE 7
BAT-1 Cures Mice Bearing B16 and 3LL Tumors

Mice inoculated with B16 melanoma cells or with 3LL cells as described above die within 25–35 days after tumor inoculation. Against this, as seen in FIG. 11, all mice that were injected with BAT-1 (10 μg/mouse) 14 days after tumor inoculation survived over 100 days. The majority of the animals which were followed up for 5 months showed no signs of illness and were free of metastasis upon pathological examination.

EXAMPLE 8
Adoptive Transfer of Splenocytes from Mice Treated with BAT-1 mAb Splenocytes from mice that had been treated with BAT-1 mAb alone or first given injections of B16 melanoma cells and then treated with BAT-1 mAb, were transferred into recipient mice. The recipient mice were inoculated either with B16 melanoma cells or with 3LL tumor cells. As seen in Table 12 below, adoptive transfer of splenocytes from the BAT-1 mAb injected mice, induced tumor regression in the tumor bearing mice receiving the transferred splenocytes. The most effective treatment was obtained when $10^8$ splenocytes of mice which were both inoculated with B16 melanoma cells and 14 days later injected with BAT-1 were adoptively transferred to recipient tumor bearing mice. As seen in Table 12, in this case, there was complete elimination of melanoma tumor cells in B16 tumor bearing recipients and pronounced tumor regression in 3LL tumor bearing recipients, as presented in the number of metastases as well as in the lung weight.

TABLE 12

Adoptive transfer induced tumor retression[a]

| Donor Group | Tumor inoculated mice (Recipients) | | | | | | | |
|---|---|---|---|---|---|---|---|---|
| | B16 | | | | 3LL | | | |
| | No. of splenocytes transferred | | | | | | | |
| | $10^7$ | | $10^8$ | | $10^7$ | | $10^8$ | |
| | No. Mets. | Lung Wt. | No. Mets. | Lung Wt. | No. Mets. | Lung Wt. | No. Mets. | Lung Wt. |
| A. untreated | >250 | 1.09 ± 0.9[c] | >250 | 1.12 ± 0.04 | >250 | 1.05 ± 0.16 | >250 | 1.12 ± 0.16 |
| B. BAT-treated[b] | 89 ± 10[d] | 0.67 ± 0.04 | 28 ± 4.3 | 0.41 ± 0.19 | 134 ± 15 | 0.87 ± 0.29 | 134 ± 19 | 0.77 ± 0.31 |
| C. B16 injected[c] and BAT treated | 4 ± 4 | 0.32 ± 0.01 | 0 ± 0.0 | 0.31 ± 0.01 | 3.6 ± 2.9 | 0.34 ± 0.06 | 2.6 ± 1.1 | 0.36 ± 0.03 |

[a]Splenocytes from three groups of mice (A, B, C) were injected i.v. into recipient mice, 14 days post tumor inoculation.
[b]Splenocytes were transferred from mice 20 days after i.v. injection of BAT (10 μg/mouse).
[c]Conditions as in [b] except that mice were inoculated with B16 melanoma 14 days prior to BAT administration.
[d]Mean number of lung metastases ± SD from three mice.
[e]Mean number of lungs weight (gr) ± SD from three mice.

These results indicated that splenocytes alone from B16 inoculated and BAT-1 treated mice exhibited anti-tumor effect against both B16 and 3LL tumors. Therefore, it seems that BAT-1 enhances non-specific cellular effector mechanisms. Furthermore, the presence of tumors potentiated the enhancement of BAT-1 induced generation of such effector cells.

We claim:

1. A monoclonal antibody or an antigen binding fragment thereof, wherein the monoclonal antibody
   i. is secreted by the hybridoma cell line deposited at the Collection Nationale de Cultures de Microorganismes (CNCM), under Accession No. I-1397, or
   ii. recognizes the same antigenic epitope as the antibody under (i).

2. A monoclonal antibody or antigen binding fragment according to claim 1, secreted by the hybridoma cell line deposited at CNCM under Accession No. I-1397.

3. An immortalized cell line secreting an antibody according to claim 1.

4. An immortalized cell line according to claim 3, which is a hybridoma cell line.

5. A hybridoma cell line according to claim 4, wherein the hybridoma cell line is deposited at the CNCM under Accession No. I-1397.

6. A method for the treatment of cancer in an individual comprising administering to said individual a therapeutically effective amount of a monoclonal antibody according to claim 1 so as to elicit an anti-tumor effect in the treated individual.

7. A method according to claim 6, wherein the monoclonal antibody is that secreted by the hybridoma cell line deposited at the CNCM under Accession No. I-1397.

8. A pharmaceutical composition comprising, as an active ingredient, a therapeutically effective amount of a monoclonal antibody according to claim 1 so as to elicit an anti-tumor effect in the treated individual, and a physiologically acceptable carrier.

9. A pharmaceutical composition according to claim 8, wherein the antibody is that secreted by the hybridoma cell line deposited at the CNCM under Accession No. I-1397.

* * * * *